United States Patent
Manhart

(10) Patent No.: US 12,229,924 B2
(45) Date of Patent: Feb. 18, 2025

(54) OPTIMUM WEIGHTING OF DSA MASK IMAGES

(71) Applicant: Siemens Healthcare GmbH, Erlangen (DE)

(72) Inventor: Michael Manhart, Fürth (DE)

(73) Assignee: Siemens Healthineers AG, Forchheim (DE)

( * ) Notice: Subject to any disclaimer, the term of this patent is extended or adjusted under 35 U.S.C. 154(b) by 392 days.

(21) Appl. No.: 17/876,104

(22) Filed: Jul. 28, 2022

(65) Prior Publication Data

US 2023/0037260 A1    Feb. 2, 2023

(30) Foreign Application Priority Data

Jul. 30, 2021  (DE) ...................... 10 2021 208 272.6

(51) Int. Cl.
*G06T 5/70* (2024.01)
*A61B 6/00* (2024.01)
(Continued)

(52) U.S. Cl.
CPC ................ *G06T 5/70* (2024.01); *A61B 6/481* (2013.01); *A61B 6/504* (2013.01); *A61B 6/5264* (2013.01);
(Continued)

(58) Field of Classification Search
CPC ....... G06T 5/70; G06T 7/0012; G06T 7/0014; G06T 7/0016; G06T 2207/20182; G06T 2207/20224; G06T 2207/30101; G06T 2207/30104; A61B 6/481; A61B 6/504; A61B 6/5264
See application file for complete search history.

(56) References Cited

U.S. PATENT DOCUMENTS

| | | | | |
|---|---|---|---|---|
| 7,852,984 B2* | 12/2010 | Zellerhoff | .............. | A61B 6/481 |
| | | | | 378/98.12 |
| 8,126,236 B2* | 2/2012 | Harer | .................... | A61B 6/481 |
| | | | | 378/98.12 |

(Continued)

FOREIGN PATENT DOCUMENTS

| DE | 102019202514 A1 | 8/2020 |
|---|---|---|
| DE | 102020214319 B3 | 1/2022 |

OTHER PUBLICATIONS

Waltz, Richard A., et al. "An interior algorithm for nonlinear optimization that combines line search and trust region steps." Mathematical programming 107.3 (2006): 391-408.

*Primary Examiner* — Scott A Rogers
(74) *Attorney, Agent, or Firm* — Lempia Summerfield Katz LLC

(57) ABSTRACT

A method for generating a subtraction image for digital subtraction angiography to reduce noise and movement artifacts. Obtaining a plurality of mask images of an object takes place before administering a contrast agent into the object and obtaining a map of the object after administering a contrast agent into the object. A first sum image is obtained from the plurality of mask images in that the plurality of mask images is summed in each case multiplied by an individual weighting. The individual weightings for each of the plurality of mask images are automatically determined by an optimization method, and the subtraction image is ascertained by subtraction of the sum image from the map.

20 Claims, 2 Drawing Sheets

(51) Int. Cl.
*A61B 6/50* (2024.01)
*G06T 5/50* (2006.01)
*G06T 7/00* (2017.01)

(52) U.S. Cl.
CPC .............. *G06T 5/50* (2013.01); *G06T 7/0016* (2013.01); *G06T 2207/20182* (2013.01); *G06T 2207/20224* (2013.01); *G06T 2207/30104* (2013.01)

(56) References Cited

U.S. PATENT DOCUMENTS

| | | |
|---|---|---|
| 10,147,171 B2 * | 12/2018 | Brown .................... A61B 6/469 |
| 10,314,557 B2 * | 6/2019 | Han ........................ A61B 6/504 |
| 10,682,110 B2 * | 6/2020 | Leghissa ................... G06T 5/50 |
| 2008/0051648 A1 | 2/2008 | Suri et al. |
| 2009/0245606 A1 | 10/2009 | Prince et al. |
| 2010/0128991 A1 | 5/2010 | Weese et al. |
| 2012/0121146 A1 | 5/2012 | Von Berg |
| 2018/0279983 A1 | 10/2018 | Ohishi |
| 2020/0273217 A1 | 8/2020 | Kaethner et al. |
| 2022/0156904 A1 | 5/2022 | Manhart |
| 2024/0095991 A1 * | 3/2024 | Manhart ................... G06T 5/50 |
| 2024/0289924 A1 * | 8/2024 | Yue .......................... G06T 7/20 |

* cited by examiner

OPTIMUM WEIGHTING OF DSA MASK IMAGES

CROSS REFERENCE TO RELATED APPLICATIONS

This patent document also claims the benefit of DE 10 2021 208 272.6 filed on Jul. 30, 2021, which is hereby incorporated in its entirety by reference.

FIELD

Embodiments relate to methods and systems for generating a subtraction image for digital subtraction angiography.

BACKGROUND

In angiography, blood vessels are depicted by diagnostic imaging methods, wherein, usually for visualization or for enhancement of the contrast in the images, a contrast agent is administered to the patient, in particular by injection. Angiography methods are used for example to examine the vascular system of patients with arteriosclerosis. In this way for example the coronary vessels of a patient are mapped to then make it possible for a doctor to make a diagnosis.

Efforts are made in angiography to stress the patient as little as possible. For this it is necessary to keep the radiation dose as low as possible. This results in the obtained images sometimes being reduced in contrast or having noise.

A further problem in angiography is that it is not just static objects that are to be examined but also dynamic objects such as the heart, the lungs or also other organs, that are affected by respiratory movements. To be able to observe the vessels sufficiently closely it is necessary in these cases to compensate the movements of the organ under consideration.

Digital subtraction angiography (DSA) is a special type of angiography. Its specific advantage in the examination of blood vessels lies in that interfering image components are rendered invisible by the subtraction. For example, a plurality of successive images is created of the body part to be examined, such as the brain. During the acquisition sequence a contrast agent is injected that spreads in the vessels. At the beginning, however, what is known as a mask image is obtained without contrast agent. What are known as fill images are subsequently created in which the contrast agent has spread to a greater or lesser extent into the vessels. The digital mask image is subtracted from the fill images. The result of the subtraction are only those image parts that are differentiated, in other words precisely the vessels supplied with blood.

In DSA imaging a series of mask images is often acquired. The mask images are averaged to obtain an optimum noise reduction. With movements of the object or body part such average values are not usually constructive.

BRIEF SUMMARY AND DESCRIPTION

The scope of the present invention is defined solely by the appended claims and is not affected to any degree by the statements within this summary. The present embodiments may obviate one or more of the drawbacks or limitations in the related art.

Embodiments reduce the noise component in a subtraction image, for example, by taking into account movements of the object to be mapped.

Embodiments provide a method for generating a subtraction image for digital subtraction angiography. The method may be used with any type of imaging in which a subtraction image is generated. The subtraction image is obtained from at least two acquisitions that were obtained under two different conditions. For example, an X-ray examination or magnetic resonance tomography and computed tomography or sonography may serve as imaging methods.

A plurality of mask images of an object is obtained before administering a contrast agent into the object. At least two mask images of the object (for example brain, heart, etc.) are created by the selected imaging method, therefore. The mask images constitute reference images that show the object in the natural state when the contrast agent has not yet spread in the object, for example in vessels. The mask images include contours, that reproduce the structure of the object, but are not of consequence or of little consequence to the examination. The mask images also include for example the vessels to be examined, although they are not shown with a very high contrast.

After administering a contrast agent into the object (for example body part) a map of the object is obtained. The map reproduces the effects of the spreading contrast agent. Administering a contrast agent is itself not part of the method. Here it is merely a matter of contrast agent being located in the vessel or the vessels when obtaining the map of the object. Since the contrast agent brings about a particularly high contrast in imaging, for example the vessels, in which the contrast agent spreads, may be identified on the map in a particularly high-contrast manner. The map of the object also includes, for example, other vessel structures, that may likewise be identified on the mask images.

A (first) sum image is subsequently formed from the plurality of mask images in that the plurality of mask images is summed in each case with an individual weighting. The advantage is that each of the plurality of mask images may be weighted very specifically. This may be advantageous in particular when mask images are obtained during different respiratory phases. In this case it is sometimes necessary to take into account the mask images of a particular respiratory phase with high weightings and to weight other mask images of other respiratory phases only slightly. In this way movements may be at least partially compensated, especially if the map (in other words one or a more fill image(s)) is created precisely during this respiratory phase.

It is accordingly of particular consequence that the individual weightings for each of the plurality of mask images are automatically determined by an optimization method. The individual weightings for the mask images are not strictly predefined therefore but are individually and automatically obtained during the course of an optimization for each mask image. In principle any optimizations, that in accordance with an optimization criterion result in the respective weightings of the plurality of mask images, are suitable for this. Such optimization methods may be based on analytical and on numerical algorithms. As a rule the optimization algorithm requires for this purpose only the mask images and a corresponding, predefined optimization criterion.

The subtraction image is ascertained by subtraction of the sum image from the map. The (optimized) sum of the weighted mask images, in other words the sum image or the optimized mask image, is therefore subtracted from the map, that is obtained from one or more of fill image(s) or corresponds thereto. The resulting subtraction image consequently includes fewer structures, that were eliminated in accordance with optimization criterion or the optimization method. The aim of the optimization method is to suppress noise and/or to compensate movements. For this a correspondingly suitable quality measure for example may be used for the optimization method.

In one embodiment it is provided that for the map a single fill image or raw image of the object is obtained after administering a contrast agent. The single raw image is therefore, for example, a fill image in which the vessels have been at least partially filled with the contrast agent. In this case only a single raw image or fill image, but a plurality of mask images, is used for optimization of the subtraction image, therefore. This is advantageous when the optimization method is run through only a single time for obtaining the optimized mask image. Further subtraction images may thus be easily obtained by way of a current fill image and the subtraction of the optimized mask image.

In an embodiment it is provided that for the map a plurality of raw images of the object is obtained after administering a contrast agent, and a second sum image is obtained from the plurality of raw images in that the plurality of raw images are summed in each case with an individual weighting, wherein the individual weightings are automatically determined for the plurality of raw images by the optimization method. This means that not only individual weightings are ascertained for the plurality of mask images, but also individual weightings for the plurality of raw images or plurality of fill images. This is advantageous when the time dynamics in the examination are less relevant. If, for example, three to seven images or even up to 30 images are obtained per second, it may thus certainly be advantageous if the map is also optimized, for example with regard to noise or movement, after administering a contrast agent. The subtraction image may thus be obtained for example from an optimized fill image and an optimized mask image. The optimization of the weightings for the fill or raw images and the optimization of the weightings for the mask images may take place in a joint optimization method. Within this method the weightings for the raw images may be optimized using the same partial optimization method as or a different partial optimization method from the weightings of the mask images. Accordingly, it may be necessary to use a different optimization criterion for the raw images than for the mask images. Sometimes the optimization criterion is also the same, however.

In an embodiment, a convex combination of all mask images is sought in the optimization method, which combination satisfies a quality criterion in respect of the subtraction image. A convex combination is characterized in the sum of all weightings is equal to 1 and each weighting may also assume a value between 0 and 1. An optimization of this kind by convex combination of the individual images may be used not just for the search for the weightings for the mask images, but also for the search for the weightings for the fill or raw images. An optimization by convex combination of the individual elements has the advantage that sometimes a standardization may be omitted. During the optimization the quality of the subtraction image is used as a criterion. In this way the weighting of the mask image may be controlled on the basis of the quality of the subtraction image.

In an embodiment it is provided that the quality criterion includes where an extreme value or a predefined value (for example threshold value) of a quality measure is attained. The extreme value may be a minimum or a maximum. As soon as the optimization method arrives at the extreme value or predefined value in respect of the quality of the subtraction image, the individual weightings of the mask images and optionally also of the fill images are produced therefrom.

For example, the quality measure may be an energy, a total variation or the softplus function. If, for example, energy is the quality measure, it may be advantageous to search for the subtraction image with the lowest energy. The weightings of the mask images are then set such that the energy of the subtraction image achieves a minimum. This manifests itself for example in that the subtraction image contains very little noise.

Alternatively, the quality measure may also be the total variation (also simply called "variation"). In this case too the total variation of the sum image should attain a minimum, whereby the pixel noise is suppressed as much as possible.

The quality measure may also contain what is known as the "softplus function", however. For example, positive values in the subtraction image may be suppressed by this activation function. The quality measure is not limited to the above-mentioned functions, however. Instead, other functions or also combinations of the functions or other functions may also be used.

In an embodiment, the object moves when obtaining the mask images, and the first sum image is an interpolated mask image of two successive mask images. This may be of consequence for example when imaging body parts that are affected by the respiratory cycle. If, for example, a fill image is obtained between complete inhalation and complete exhalation and in each case a mask image exists with complete inhalation and complete exhalation, it is advantageous if by way of interpolation a mask image is generated from the two mask images, that corresponds to the respiratory phase of the fill image. In this way a reliable subtraction image may be obtained. In this case the optimization method may result for example in identical weightings of the two mask images.

In another aspect, an apparatus for generating a subtraction image for digital subtraction angiography is provided, including an image acquisition facility for obtaining a plurality of mask images of an object before administering a contrast agent into the object and for obtaining a map of the object after administering a contrast agent into the object, and a computing facility for forming a first sum image from the plurality of mask images in that the plurality of mask images is summed in each case with an individual weighting, wherein the individual weightings for each of the plurality of mask images are automatically determined by an optimization method, and for ascertaining the subtraction image by subtraction of the sum image from the map.

The image acquisition facility may include a corresponding control unit that includes for example one or a plurality of processor(s) in order to control the image acquisition of the mask images and of the map of the object. Similarly, the computing facility may include a processor with which the sum image is ascertained and the weightings are obtained and the subtraction image is ascertained in the optimization method.

In another aspect, a computer program is provided, moreover, that may be loaded directly into a memory of the above-mentioned apparatus, having instructions in order to execute the steps of the above-mentioned method when the program is executed in the apparatus. The method described in the present document may therefore also be in the form of a computer program (product), that implements the method on a control unit when it is executed on the control unit. Similarly, an electronically readable data carrier with electronically readable control information stored thereon may be provided, that includes at least one computer program of the above type and is configured in such a way that it carries out a method of the type mentioned above when the data carrier is used in a control facility of the above-mentioned apparatus.

DETAILED DESCRIPTION

Figure 1:
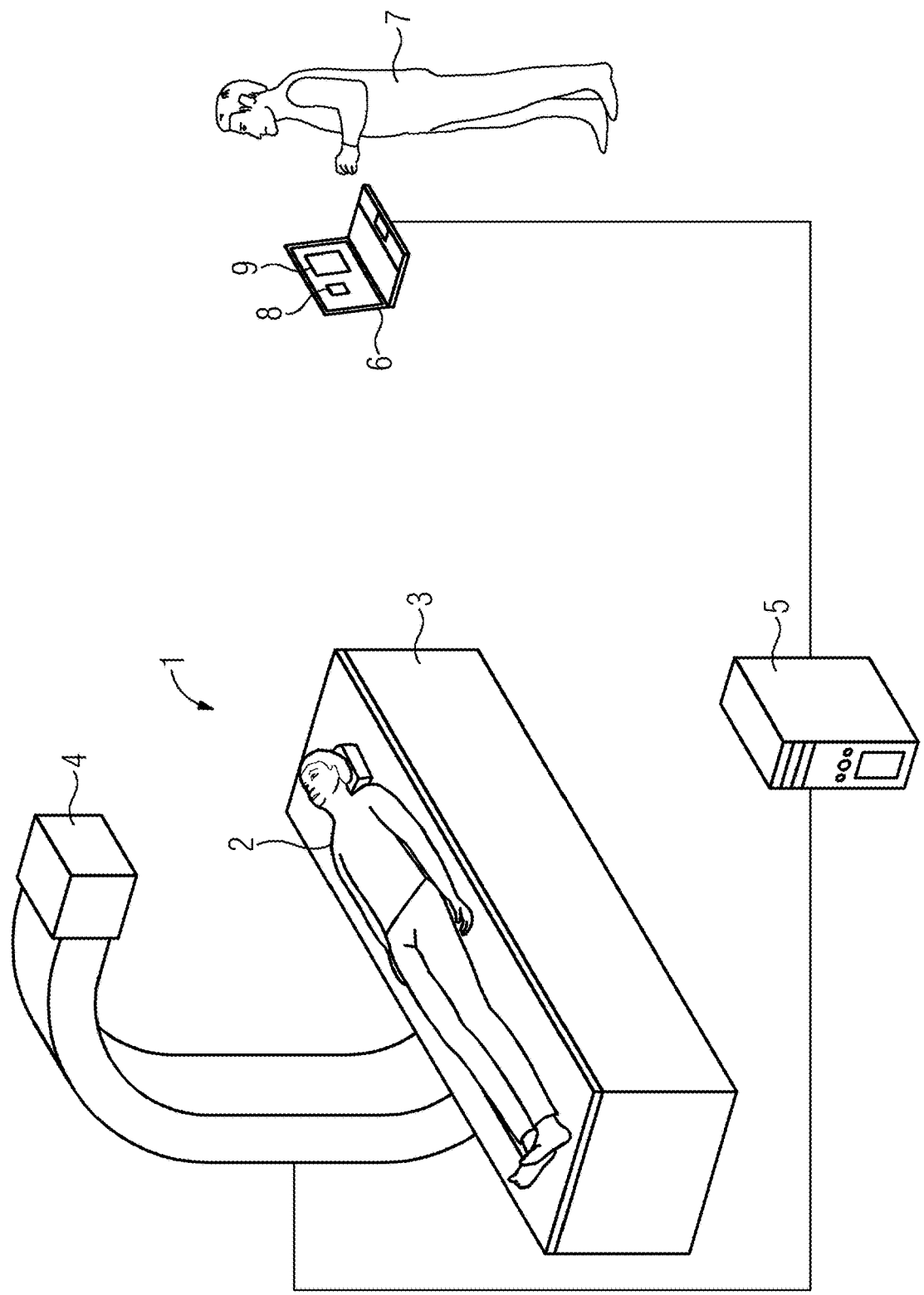
FIG. 1 depicts a facility for digital subtraction angiography according to an embodiment.

FIG. 1 depicts a facility 1 for digital subtraction angiography for carrying a method for generating a subtraction image for digital subtraction angiography. In the case illustrated here a patient 2, from which digital subtraction angiography acquisitions of the leg region are to be created, is located on a patient couch 3 of the facility 1. For image acquisition the facility 1 has a C-arm system 4 with a radiation source and a detector, that is connected to a control and/or computing facility 5 and to an image output 6, via which operating inputs are also possible. In this embodiment, the image acquisitions may be created completely automatically, for example after an initial start by an operator 7, on the part of the control and/or computing facility 5.

This means that once the operator 7 has triggered the image acquisition once, firstly an acquisition is automatically created in a first position of the detector, opposite which the radiation source of the C-arm system 4 is arranged. Thereafter, completely automatically or manually, a contrast agent is administered to the patient 2, whereupon an acquisition (raw or fill image) takes place again in the same detector position.

The implementation of the method may be initiated by the operator 7, for example by selecting a corresponding starting field 8 on the image output 6, for example via the keyboard or a computer mouse or the like.

The image acquisitions, that are produced in the individual detector positions as a result of a subtraction or as an intermediate step in the acquisitions, may be depicted on the image output 6 as acquisitions 9 for checking, that accompanies an examination, by the operator 7 or for subsequent evaluation likewise. The image data and further data, that is ascertained during the course of implementation of the method, may in addition optionally be stored in the control and/or computing facility 5 to subsequently be evaluated, for example by a doctor, or be sent via an intranet or the Internet to further or external computers.

In the present embodiment of DSA imaging, a series of mask images is acquired. To obtain optimum noise suppression and to compensate movements (for example respiratory movements), it may be advantageous to use a weighting, that weights mask images with similar movement phase to the fill image more highly.

In order to eliminate movement artifacts, instead of averaging a plurality of mask images, an individual mask image could be allocated to each fill image by evaluating an Image Quality Metric (IQM). If the respiratory phase of the fill image lies between the respiratory phases of two mask images, the result may be improved further by time interpolation between the two most appropriate mask images.

These methods are not yet based on cases of a plurality of mask images with the same respiratory phase or cases with little movement, however. In such cases no optimum noise reduction would be produced here that could be achieved by averaging a plurality of mask images or difference in movement. Therefore, a method is being proposed, that for all cases and for each fill image calculates an optimized, weighted averaging of the mask images. Consequently, an optimized combination of movement artifact and noise reduction may be achieved.

From a fill image F a subtraction image S may be calculated by subtraction of the mask image M. In the present case, M represents the weighted averaging of all mask images $M_i$ in accordance with the optimized weighting factors $\alpha_i$. The fill image F may also be a weighted averaging of individual fill images $F_i$ with optimized weighting factors $\beta_i$. Subsequently only the case where a single fill image F and a plurality of mask images $N_i$ are used will be considered, however. The use of a plurality of (optimally) weighted fill images is analogously produced therefrom.

The weightings $\alpha_i$ are obtained by the solution of the following non-linear optimization problem with additional conditions:

$S=F-\Sigma_i\alpha_i M_i$ with the optimization criterion argmin
$\text{IQM}(F-\Sigma_i\alpha_i M_i)$ on the condition that $\Sigma_i\alpha_i=1$
$0\leq\alpha_i\leq 1$ A convex combination (compare above conditions for $\alpha_i$) of all mask images $M_i$ is sought therefore, that delivers an optimum quality measure IQM applied to the subtraction image S. Specifically, a combination is sought here in which the quality measure attains a minimum. Alternatives are also conceivable, however, in which the quality measure attains a maximum or a different predefined value. Optimum masking may be achieved in movement phases with such an optimization of the weightings of the mask images. Furthermore, an interpolation between mask images may be achieved with this type of weighting optimization. Finally, the optimized weightings may also be used for averaging mask images with similar respiratory phase for noise reduction.

Typically, convex functions such as the energy (I2), the Total Variation (TV) or the softplus function (SP) may be used as a quality measure IQM, that suppresses positive values in the subtraction image S. Combinations of these functions may also be used as a quality measure.

Terms of the above-mentioned functions and their partial derivations are indicated below according to the weightings in order to achieve optimizations with gradient-based methods:

$$I2(S) = \sum_j (S_j)^2 \frac{\partial I2(S)}{\partial \alpha_i} = -2\sum_j S_j M_{i,j}$$

$$TV(S) =$$

-continued $$\sum_j \sqrt{S_{x,j}^2 + S_{y,j}^2 + \varepsilon} \frac{\partial TV(S)}{\partial \alpha_i} = -\sum_j (S_{x,j} \cdot M_{x,i,j} + S_{x,j} \cdot M_{y,i,j})/TV(S)_j$$

$$SP(S) = \sum_j \frac{\ln(1 + e^{k \cdot S_j})}{k} \quad \frac{\partial SP(S)}{\partial \alpha_i} = -\sum_j \frac{M_{i,j}}{1 + e^{-k \cdot S_j}}$$

In this case $S_j$ designates the pixel value of the subtraction image S at the pixel j, where j is a vector index or a two-dimensional coordinate. $M_{i,j}$ designates the pixel value of the mask image $M_i$ at pixel j. $S_{x,j}$ designates a gradient image, namely the subtraction image S derived in the x direction. Correspondingly $S_{y,j}$ denotes the derivation of the subtraction image in the y direction at pixel j. $\varepsilon$ represents a fixed offset value. $M_{x,i,j}$ and $S_{x,j}$ respectively and $M_{y,i,j}$ and $S_{y,j}$ respectively designate the pixel value of the gradient of the respective mask image $M_i$ and subtraction image S respectively at the pixel j in the x- and y-direction respectively.

The optimization problem may be efficiently solved for example with an inner-point algorithm. An algorithm of this kind is described for example in: Waltz, Richard A., et al. "An interior algorithm for non-linear optimization that combines line search and trust region steps", Mathematical Programming 107.3 (2006; pages 391-408). Other optimization algorithms may also be used, however. One implementation is provided for example by the function "fmincon" from the "Matlab" math program. A good solution may be found within two to twenty iterations already, approx. 3 s computing time, with this kind of algorithm.

Figure 2:
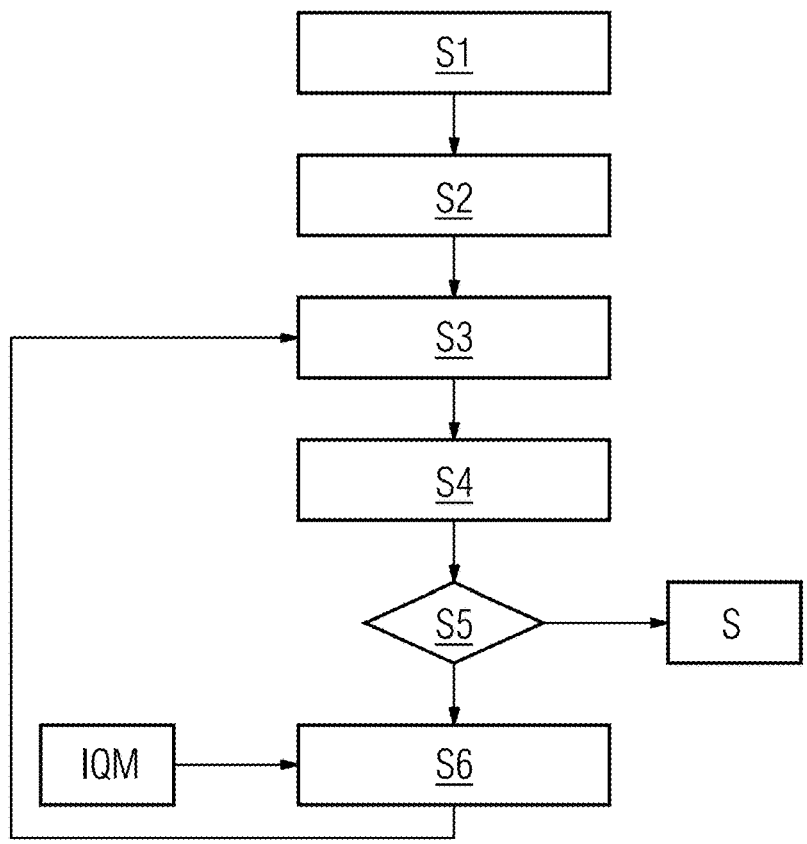
FIG. 2 depicts a schematic block diagram of a method for generating a subtraction image for digital subtraction angiography according to an embodiment.

FIG. 2 depicts a schematic block diagram of an embodiment of a method. In a first step S1 a plurality of mask images $M_i$ of an object is obtained before administering a contrast agent into the object. In a second step S2 a map or a fill image F of the object is obtained after administering a contrast agent into the object. A plurality of fill images $F_i$ is also obtained by corresponding weighting in this step for creating the map. In a subsequent step S3 a sum image $\Sigma_i \alpha_i M_i$ is formed from the plurality of mask images $M_i$ in that the plurality of mask images $M_i$ is summed in each case multiplied by an individual weighting $\alpha_i$. In step S4 the subtraction image S is then ascertained by subtraction of the sum image $\Sigma_i \alpha_i M_i$ from the map F. In a subsequent step S5 it is checked whether the optimization algorithm has attained its optimization target. If so, the subtraction image S is output. If the target has not yet been attained step S6 is carried out. A (renewed) iteration of an optimization algorithm is executed in this case. For this a quality measure IQM in respect of the subtraction image is used for optimization. After the optimization iteration in step S6 the process returns to step S3 again. An optimized subtraction image S results from the optimization loop S3-S6.

Figure 3:
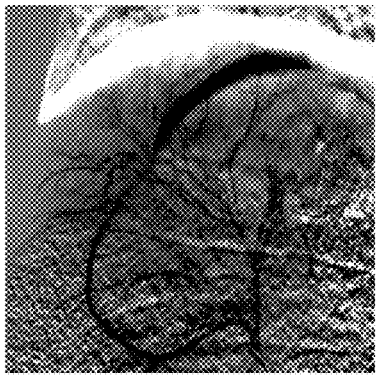
FIG. 3 depicts a subtraction image of a pig's liver with mask averaging according to an embodiment.

FIGS. 3 to 8 show DSA subtraction images with which the advantage of the optimization method may be illustrated. FIGS. 3 to 8 thus each show subtraction images of a pig's liver during respiratory movements. FIG. 3 depicts a subtraction image with simple mask averaging, whereby a good noise level may be achieved in particular with a low-dose dataset. Severe movement artifacts may be seen, however, in particular in the upper part of the image.

Figure 4:
FIG. 4 depicts the subtraction image of FIG. 3, but with mask adjustment according to an embodiment.

FIG. 4 depicts a subtraction image in which the mask image has been adjusted to the movement phase of the fill image. This produces an improved reduction in movement artifacts but also a higher noise level in the low-dose dataset.

Figure 5:
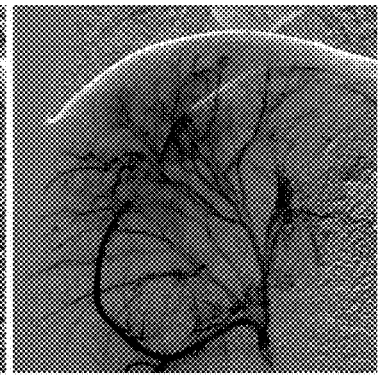
FIG. 5 the subtraction image of FIG. 2 with optimized mask weighting according to an embodiment.

FIG. 5 depicts a subtraction image with inventively optimized mask weighting. Advantages may be attained with this weighting optimization both in the reduction of movement artifacts and in the reduction of noise.

Figure 6:
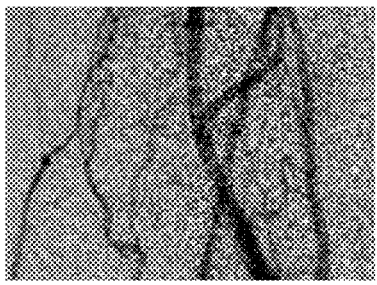
FIG. 6 depicts a subtraction image of a section of a rabbit's head with mask averaging according to an embodiment.
Figure 7:
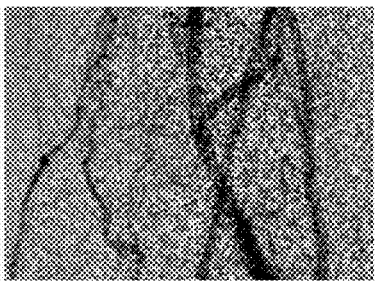
FIG. 7 depicts the subtraction image of FIG. 6 with mask adjustment according to an embodiment.
Figure 8:
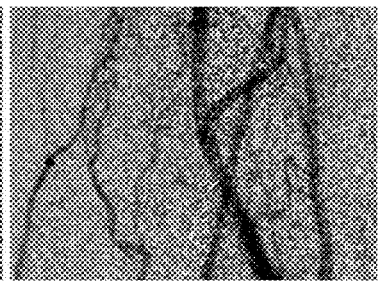
FIG. 8 depicts the subtraction image of FIG. 6 with optimized mask weighting according to an embodiment.

FIGS. 6 to 8 show DSA subtraction images of a section of a rabbit's head with low radiation dose. Here too FIG. 6 depicts the subtraction image with simple mask averaging to reduce the noise level.

FIG. 7 depicts a subtraction image with mask adjustment to the respective movement state. The higher noise level compared to FIG. 6 may be seen again here. Finally FIG. 8 depicts a subtraction image with optimized weighting of the plurality of mask images. With improved reduction of movement artifacts the noise level is also reduced here compared to FIG. 7.

The above embodiments present a method therefore, that, by solving an optimization problem with additional conditions for each fill image or for an optimized fill image, calculates an optimized, weighted averaging of the mask images. An improved combination of movement artifact and noise reduction may consequently be achieved.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for generating a subtraction image for digital subtraction angiography, the method comprising:
   obtaining a plurality of mask images of an object before administering a contrast agent into the object;
   obtaining a map of the object after administering a contrast agent into the object;
   forming a first sum image from the plurality of mask images, wherein the plurality of mask images is summed in each case multiplied by an individual weighting, wherein the individual weightings for each of the plurality of mask images are automatically determined by an optimization method; and
   ascertaining the subtraction image by subtraction of the sum image from the map.

2. The method of claim 1, wherein for the map a single raw image of the object is obtained after administering a contrast agent.

3. The method of claim 1, wherein for the map a plurality of raw images of the object is obtained after administering a contrast agent, and a second sum image is obtained from the plurality of raw images in that the plurality of raw images are summed in each case with an individual weighting, wherein the individual weightings for the plurality of raw images are automatically determined by the optimization method.

4. The method of claim 1, wherein in the optimization method a convex combination of all mask images is sought, which satisfies a quality criterion in respect of the subtraction image.

5. The method of claim 4, wherein the quality criterion consists in that an extreme value or a predefined value of a quality measure is attained.

6. The method of claim 5, wherein the quality measure is an energy, a total variation or the softplus function.

7. The method of claim 1, wherein the object moves when obtaining the mask images and the first sum image is an interpolated mask image of two successive mask images.

8. An apparatus for generating a subtraction image for digital subtraction angiography, the apparatus comprising:
an image acquisition facility configured to obtain a plurality of mask images of an object before administering a contrast agent into the object and to obtain a map of the object after administering a contrast agent into the object; and
a computing facility configured to form a first sum image from the plurality of mask images in that the plurality of mask images are summed in each case with an individual weighting, wherein the individual weightings for each of the plurality of mask images are automatically determined by an optimization method, the computing facility further configured to ascertain the subtraction image by subtraction of the sum image from the map.

9. The apparatus of claim 8, wherein for the map a single raw image of the object is obtained after administering a contrast agent.

10. The apparatus of claim 8, wherein for the map a plurality of raw images of the object is obtained after administering a contrast agent, and a second sum image is obtained from the plurality of raw images in that the plurality of raw images are summed in each case with an individual weighting, wherein the individual weightings for the plurality of raw images are automatically determined by the optimization method.

11. The apparatus of claim 8, wherein in the optimization method a convex combination of all mask images is sought, which satisfies a quality criterion in respect of the subtraction image.

12. The apparatus of claim 11, wherein the quality criterion consists in that an extreme value or a predefined value of a quality measure is attained.

13. The apparatus of claim 12, wherein the quality measure is an energy, a total variation or the softplus function.

14. The apparatus of claim 8, wherein the object moves when obtaining the mask images and the first sum image is an interpolated mask image of two successive mask images.

15. A non-transitory computer readable storage medium comprising a set of computer-readable instructions stored thereon for generating a subtraction image for digital subtraction angiography, the instructions which, when executed by at least one processor cause the processor to:
obtain a plurality of mask images of an object before administering a contrast agent into the object;
obtain a map of the object after administering a contrast agent into the object;
form a first sum image from the plurality of mask images, wherein the plurality of mask images is summed in each case multiplied by an individual weighting, wherein the individual weightings for each of the plurality of mask images are automatically determined by an optimization method; and
ascertain the subtraction image by subtraction of the sum image from the map.

16. The non-transitory computer readable storage medium of claim 15, wherein for the map a single raw image of the object is obtained after administering a contrast agent.

17. The non-transitory computer readable storage medium of claim 15, wherein for the map a plurality of raw images of the object is obtained after administering a contrast agent, and a second sum image is obtained from the plurality of raw images in that the plurality of raw images are summed in each case with an individual weighting, wherein the individual weightings for the plurality of raw images are automatically determined by the optimization method.

18. The non-transitory computer readable storage medium of claim 15, wherein in the optimization method a convex combination of all mask images is sought, which satisfies a quality criterion in respect of the subtraction image.

19. The non-transitory computer readable storage medium of claim 18, wherein the quality criterion consists in that an extreme value or a predefined value of a quality measure is attained.

20. The non-transitory computer readable storage medium of claim 19, wherein the quality measure is an energy, a total variation or the softplus function.

* * * * *